United States Patent [19]

Buss et al.

[11] Patent Number: 5,045,557
[45] Date of Patent: Sep. 3, 1991

[54] IMIDAZABLE FUNGICIDES AND USE THEREOF

[75] Inventors: Antony D. Buss, Amersham; Philip J. Dudfield; John H. Parsons, both of Saffron Walden, all of England

[73] Assignee: Schering Agrochemicals Ltd., England

[21] Appl. No.: 573,723

[22] Filed: Aug. 28, 1990

Related U.S. Application Data

[63] Continuation-in-part of Ser. No. 169,845, Mar. 18, 1988, abandoned.

[30] Foreign Application Priority Data

Mar. 21, 1987 [GB] United Kingdom ............... 8706679
Sep. 22, 1987 [GB] United Kingdom ............... 8722329

[51] Int. Cl.$^5$ .................... A01N 43/50; C07D 233/90
[52] U.S. Cl. ..................................... 514/398; 548/337
[58] Field of Search ......................... 548/337; 514/398

[56] References Cited

FOREIGN PATENT DOCUMENTS 298196  1/1989  European Pat. Off. ............ 548/337

Primary Examiner—Mary C. Lee
Assistant Examiner—Patricia L. Morris
Attorney, Agent, or Firm—Ostrolenk, Faber, Gerb & Soffen

[57] ABSTRACT

The invention provides compounds of formula I

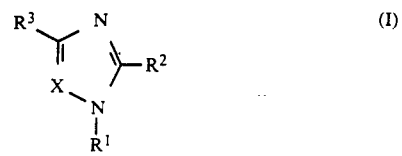

in which X, $R^1$, $R^2$ and $R^3$ are as defined in the description. The compounds have valuable fungicidal activity.

12 Claims, No Drawings

IMIDAZABLE FUNGICIDES AND USE THEREOF

This is a continuation-in-part of application Ser. No. 07/169,845, filed Mar. 18, 1988, now abandoned.

This invention relates to compounds having fungicidal activity.

According to the invention there is provided a compound of formula I

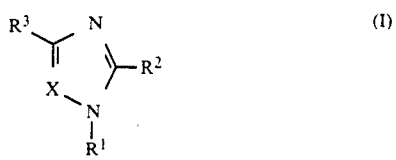

in which
X is $CR^4$ or N:
$R^1$ is $-SO_2R^5$,

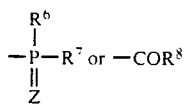

$R^2$ is CN,

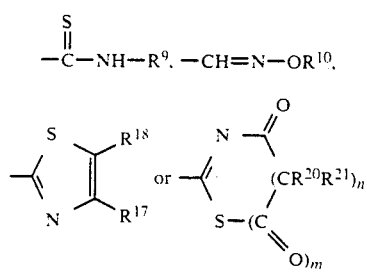

$R^3$ and $R^4$, may be the same or different and are alkyl, cycloalkyl, cycloalkenyl, alkenyl, alkynyl or amino, all of which are optionally substituted, hydrogen, halogen, hydroxy, cyano, nitro, acyl, $R^{11}SO_p$, $R^{12}O$ or aryl;
$R^5$ is aryl, optionally substituted alkyl or optionally substituted amino;
$R^6$ and $R^7$, may be the same or different and are amino, alkoxy or alkylthio, each of which is optionally substituted:
$R^8$ has the same meaning as $R^5$ or can be alkoxy, alkenyloxy, alkynyloxy or alkylthio, each of which is optionally substituted, or is aryloxy;
$R^9$ is hydrogen optionally substituted alkyl, alkenyl, alkynyl, alkoxyoarbonyl, acyl, aryl or cycloalkyl;
$R^{10}$ is hydrogen, optionally substituted alkyl, alkenyl or alkynyl;
$R^{11}$ is alkyl, cycloalkyl, cycloalkenyl, alkenyl, alkynyl, all of which are optionally substituted, or is aryl;
$R^{12}$ has the same meaning as $R^{11}$ or is acyl;
$R^{17}$ is hydrogen, alkyl, alkoxycarbonyl, aryl or heteroaryl and $R^{18}$ is hydrogen or alkyl or $R^{17}$ and $R^{18}$ together with the carbons to which they are attached, form a benzo ring:
$R^{20}$ and $R^{21}$ may be the same or different and are hydrogen or alkyl;
Z is oxygen or sulphur;
m is 0 and n is 1 or 2 or m is 1 and n is 0 or 1; and
p is 0 or 1,
with the proviso that $R^3$ and $R^4$ cannot both be chlorine.

Alkyl and alkoxy groups are preferably of 1 to 8 carbon atoms, especially methyl, and alkenyl and alkynyl groups are usually of 3 to 4 carbon atoms. Substituents, when present on any such group, include halogen, hydroxy, alkoxy and aryl. Aryl groups are usually phenyl, optionally substituted, e.g. by halogen, alkyl, alkoxy, nitro, cyano, $-COR^8$, optionally substituted sulphamoyl, optionally substituted amino, alkyl-$SO_q$, or aryl-$SO_q$, where q is 0, 1 or 2, and any alkyl or alkoxy group is optionally substituted.

The term aryl may include heteroaryl groups such as thienyl, furyl or pyridyl and can also include polynuclear aromatic groups, such as naphthyl and benzimidazolyl. The term acyl can include residues of both carboxylic and sulphonic acids and includes the groups $R^{13}(O)_rCO$ and $R^{13}SO_2$, where $R^{13}$ has the same meaning as $R^{11}$, or is optionally substituted amino and r is 0 or 1. It thus includes residues of carbamic and sulphamic acids. Acyl groups are preferably alkanoyl, aroyl, alkylsulphonyl, arylsulphonyl, N,N-dialkylsulphamoyl or N-alkyl-N-arylsulphamoyl, in which the alkyl groups are e.g. of 1 to 4 carbon atoms, and the alkyl and phenyl can be substituted as previously mentioned. Amino groups are usually substituted by one or more of the groups $R^{11}$, acyl, optionally substituted amino (including groups substituted through a double bond), hydroxy or optionally substituted alkoxy, or two substituents can form a ring, e.g. a morpholino or piperidino ring. Sulphamoyl groups can be substituted similarly to amino groups. Cycloalkyl groups are usually of 3 to 8 carbon atoms especially cyclopentyl or cyclohexyl.

$R^1$ is generally a substituted sulphamoyl group, especially dimethylsulphamoyl. $R^2$ is preferably cyano or thiocarbamoyl. When X is $CR^4$, $R^4$ is preferably hydrogen, but may be cyano, methyl or ethoxyalkyl. $R^3$ is preferably phenyl or benzoyl, optionally substituted by up to three groups, selected from halogen, alkyl (especially methyl), trifluoromethyl, nitro and alkoxy (especially methoxy).

The compounds of the invention have activity as fungicides, especially against fungal diseases of plants, e.g. downy mildews, especially vine downy mildew (Plasmopara viticola), and late tomato blight and potato blight (Phytophthora infestans). They are also active against powdery mildews, such as barley powdery mildew (Erysiphe graminis), as well as being active against diseases such as rice blast (Pyricularia oryzae) and apple scab (Venturia inaequalis). They may also have activity against other fungi, such as Botrytis spp., Puccinia spp., Rhizoctonia spp., Fusarium spp. and Pythium spp.

The invention thus also provides a method cf combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition the composition can comprise one or more additional active ingredients, for example compounds known to possess plant-growth regulant, herbicidal, fungicidal,insecticidal or acaricidal properties. Alternatively the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates: lignin sulphonates: petroleum sulphonates: alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound o the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.01 to 3.0 per cent by weight, especially 0.01 to 1.0 per cent by weight. In a primary composition the amount of active ingredient can vary widely and can be, for example, from 5 to 95 per cent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in !he same drill as the seeds. A suitable application rate is within (he range of from 0 05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg per hectare.

The compounds of the invention may be prepared, in known manner, in a variety of ways. Where $R^2$ is cyano, the compounds can be prepared by cyanation of a compound of formula II

This can be achieved for instance by reacting the compound of formula II with a compound CN-Z, where Z is a leaving group, such as cyano or p-tosyl. This reaction is generally carried out in the presence of a stong base and preferably an alkyl metal, such as butyllithium. The cyanation can also be carried out by (i) fermylating a compound of formula II, (e.g. using dimethylformamide in the presence of strong base, such as butyllithium) to give a compound of formula I in which $R^2$ is formyl, (ii) treating this compound with hydroxylamine and (iii) subsequently dehydrating the oxime so obtained to give the desired compound of formula I, in which $R^2$ is cyano. Dehydration may be achieved using a reagent such as trifluoroacetic anyhydride or a chloroformate ester, under alkaline conditions. In the latter case an ester group may be substituted onto the 1-position.

Compounds, where $R^2$ is $-CH=N-OR^{10}$, can be obtained in a similar manner to steps (i) and (ii) above, using a compound of formula $H_2N-OR^{10}$.

Compounds of the invention can also be obtained by reacting a compound of formula III

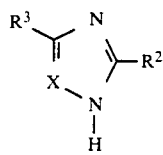
(III)

in which $R^2$ is as defined above, except for thiocarbamoyl, with a compound of formula $R^1Q$, where Q is a leaving group, such as halogen, especially chlorine.

Compounds of formula I, where $R^2$ is cyano, can be modified in known manner to give compounds where $R^2$ is thiocarbamoyl, by reaction with hydrogen sulphide and if desired modifying this group in known manner to give compounds where $R^9$ is not hydrogen or to give compounds where $R^2$ is

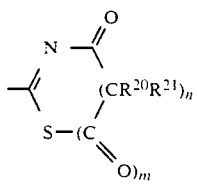

These reactions are usually carried out using a suitable acyl halide or isocyanate, for instance as described in EP 219192.

Compounds of formula I, where X is $CR^4$, where $R^4$ is other than hydrogen may also be obtained in known manner by reacting the compound where $R^4$ is hydrogen with a compound, $R^4-W$, where W is a leaving group, such as halo (especially iodo or chloro) or p-tosyl. This reaction is generally carried out in the presence of a strong base, preferably an alkyl metal, such as butyllithium.

Compounds where $R^3$ is a alkanoyl or aroyl group can be prepared by oxidising a compound of formula IV

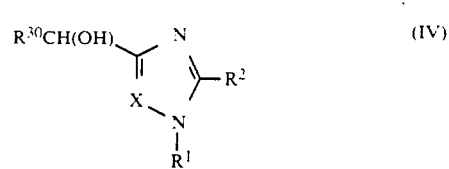
(IV)

in which $R^{30}$ is the alkanoyl or aroyl group minus the carbonyl, e.g. using a dichromate, such as pyridinium dichromate.

Compounds of formula II or III are known or can be obtained in a variety of known ways, for instance using methods as described for the preparation of starting materials hereinafter.

Compounds of formula IV can be obtained by removing the protecting group from a compound of formula V

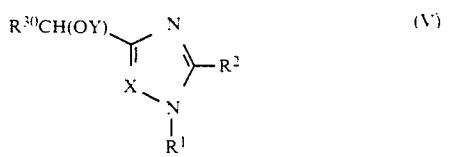
(V)

where y is a protecting group such as a trialkylsilyl.

Compounds of formula V can in their turn be prepared by cyanation etc. as described above, of the compounds of formula V in which $R^2$ is hydrogen. These compounds can in their turn be prepared according to the following reaction scheme.

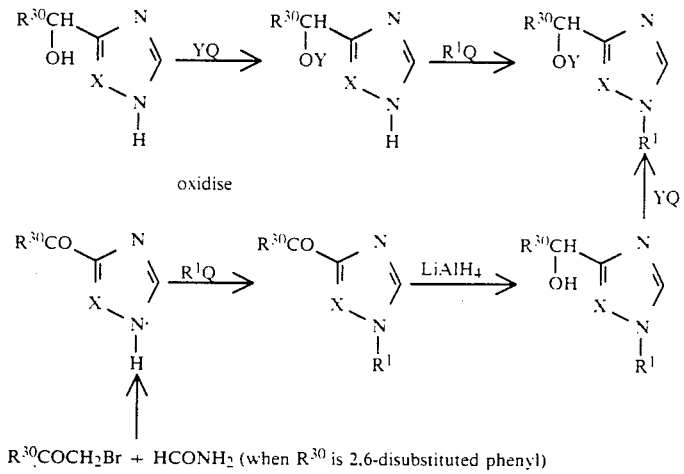

$R^{30}COCH_2Br + HCONH_2$ (when $R^{30}$ is 2,6-disubstituted phenyl)

The invention is illustrated in the following Examples. Structures of isolated novel compounds were confirmed by elemental and/or other appropriate analyses. Temperatures are in °C. and are uncorrected.

EXAMPLE 1 a) To 4-(2,4-Dichlorophenyl)-1-(dimethylsulphamoyl)imidazole, (8.0 g) in tetrahydrofuran (125ml), maintained under a dry nitrogen atmosphere at −60° was added 2.6M butyllithium in hexane (10.57 ml). The solution was stirred and after a short time dimethylformamide (2.9 ml) was added. The mixture was warmed slowly to room temperature and then added to dilute hydrochloric acid. The product was extracted with ethyl acetate and the extract washed with water, dried the solvent evaporated and the solid residue recrystallised from toluene to give 4-(2,4-dichlorophenyl)-1-(dimethylsulphamoyl)-2-formylimidazole, m.p. 148°–157° (dec.).

b) This product (6.26 g) was added to a mixture of hydroxylamine hydrochloride (1.26 g) and sodium acetate (1.48 g) in 95% ethanol (45ml), followed by addition of tetrahydrofuran (20ml). The mixture was heated on a steam bath for two minutes, filtered and the solid remaining was washed with acetone. The filtrate and washings were combined and the solvent evaporated under reduced pressure. The residue was washed with water and dried over phosphorus pentoxide to give 4-(2,4-dichlorophenyl)-1-(dimethylsulphamoyl)-2-(hydroxyiminomethyl)imidazole. m.p. 145°–157° (dec.).

c) To this product (6.26 g) in pyridine (4.24 ml) and dioxane (8 ml) was added trifluoroacetic anhydride (1.88 ml) with stirring and cooling on an ice bath. After stirring for 5 hours at room temperature the mixture was added to ice-water and the solid collected by filtration. This was recrystallised from toluene to give 2-cyano-4-(2,4-dichlorophenyl)-1-(dimethylsulphamoyl)imidazole, m.p. 161°–4° (dec.). (Compound 1)

EXAMPLE 2

This example illustrates an alternative method of preparing compound 1.

To a solution of 4-(2,4-dichlorophenyl)-1-(dimethylsulphamoyl)imidazole (1.62 g) in dry tetrahydrofuran (30 ml) at −70° under a dry nitrogen atmosphere was added 2.5M butyllithium in hexane (2 ml). After stirring for 15 mins, a solution of redistilled tosyl cyanide in dry tetrahydrofuran (7 mmol) was added and the reaction flask placed in an ice bath. The mixture was stirred for 30 mins, poured into water and the precipitate filtered and recrystallised to give compound 1.

EXAMPLE 3

Hydrogen sulphide was bubbled through a stirred suspension of compound 1 (1.73 g) from Example 1 in triethylamine (0.7 ml) and pyridine (10 ml) with stirring and cooling in an ice bath for 30 minutes. The mixture was poured into ice-water and the solid collected by filtration, then dried over phosphorus pentoxide to give 4-(2,4-dichlorophenyl)-1-dimethylsulphamoyl-2-thiocarbamoylimidazole, m.p. 184°–7°. (Compound 2)

EXAMPLE 4

In a similar manner to that described in Example 1, there was obtained, in turn a) 1-(dimethylsulphamoyl)-2-formyl-4-phenylimidazole: and b) 1-(dimethylsulphamoyl)-2-(hydroxyiminomethyl)-4-phenylimidazole, m.p 165°–170° (dec.). A slurry of this product (0.882 g) in dry tetrahydrofuran (20 ml) was added to sodium hydride (90 mg of 80g suspension in oil) in dry tetrahydrofuran. After 1.5 hours at room temperature ethyl chloroformate (0.285 ml) was added and the mixture stirred overnight. The mixture was then added to ethyl acetate and worked up in conventional manner to give a viscous oil. This was purified by flash column chromatography to give 2-cyano-1-ethoxycarbonyl-3-phenylimidazole, m.p. 109°–111°. (Compound 3)

EXAMPLE 5

Dimethylsulphamoyl chloride (0.54 ml) was added to a mixture of 2-cyano-4-(2-nitrophenyl)-1H-imidazole (0.865 g) and sodium hydride (150 mg of 80% in oil). The mixture was heated under reflux for one hour and then poured into ice/water and extracted with ethyl acetate. The extract was washed with brine, dried and evaporated. The residual oil slowly solidified and was washed with ether and filtered to give 2-cyano-1-(dimethylsulphamoyl)4-(2-nitrophenyl)imidazole, m.p. 111°–4°. (Compound 4)

EXAMPLE 6

Butyllithium (2.5M; 2 ml) was added to a solution of 1-(dimethylsulphamoyl)-4-(2,4,6-trichlorobenzoyl)imidazole (1.77 g) in tetrahydrofuran (25 ml), maintained at −78°. The solution was stirred for 15 minutes and cyanogen was bubbled in allowing the temperature to rise to 10°. The mixture was evaporated and purified by column chromatography, followed by trituration with diisopropyl ether to give 2-cyano-1-(dimethylsulphamoyl)-4-(2,4,6-trichlorobenzoyl)imidazole, m.p. 142°–50°. (Compound 5).

EXAMPLE 7

A solution of 2-cyano-4-(2,4-dichlorophenyl)imidazole (1.0 g) in tetrahydrofuran (30 ml) was treated with sodium hydride (0.16 g of 80% dispersion in oil) at 0°. A solution of tetramethylphosphorodiamidic chloride (0.89 g) in tetrahydrofuran (10 ml) was added dropwise and the mixture stirred for 1½ hours under nitrogen. It was then poured into water, stirred, and the precipitate filtered, dried and recrystalllsed from toluene/hexane to give 1-[bis(dimethylamino)phosphinyl]-2-cyano-4-(2,4-dichlorophenyl)imidazole, m.p. 140.5°–1°. (Compound 6).

EXAMPLE 8

Oxalyl chloride (0.23 ml) was added to a stirred solution of compound 2 (0.95g) in acetone (15ml) kept cool in an ice-salt bath. The yellow precipitate, which formed, was filtered, washed with acetone and dried to give 2-[4-(2,4-dichlorophenyl)-1-(dimethylsulphamoyl)imidazol-2-yl]thiazole-4,5-dione, m.p. 158°, (dec.). (Compound 7)

EXAMPLE 9

Butyllithium (1.67 ml of 2.5M solution in hexane) was added under a dry nitrogen atmosphere to a solution of compound 1 (1.38 g) in tetrahydrofuran (20 ml) maintained at −78°. After stirring at this temperature for 20 minutes, methyl iodide (0.8 ml) was added. The mixture was allowed to warm to room temperature and then poured into water. The aqueous phase was extracted with ethyl acetate and the extract dried and evaporated. The residual oil was purified by flash column chromatography using an ethyl acetate/hexane mixture as eluent, to give 2-cyano-4-(2,4-dichlorophenyl)-1-(dimethylsulphamoyl)-5-methylimidazole, m.p. 92°–5°. (Compound 8)

EXAMPLE 10

This example illustrates an alternative method of preparing compound 5.

2-Cyano-1-(dimethylsulphamoyl)-4-(2,4,6-trichloro-α-hydroxybenzyl)imidazole (15.7 g) was dissolved in dichloromethane and pyridinium dichromate (28.9 g) and silica gel (230–400 mesh; 58 9) added and the mixture stirred for 11 hours. The mixture was filtered and the precipitate washed with dichloromethane. The filtrate and washings were evaporated under reduced pressure and the residue washed with diisopropyl ether and dried under reduced pressure to give 2-cyano-1-(dimethylsulphamoyl)4-(2,4,6-trichlorobenzoyl)imidazole, m.p. 142°–151°. (Compound 5).

EXAMPLE 11

1-(Dimethylsulphamoyl)-2-formyl-4-(2,3,4-trichlorophenyl)imidazole was reacted with O-allylhydroxylamine hydrochloride in a similar manner to the reaction with hydroxylamine hydrochloride described in Example 1, to give 2-allyloxyiminomethyl-1-(dimethylsulphamoyl)-4-(2,3,4-trichlorophenyl)imidazole, m.p. 87°–88°. (Compound 9)

The starting material was prepared in a similar manner to that described in Example 1.

EXAMPLE 12

In a similar manner to that described in one of the previous Examples, the following compounds were obtained: The Example me(hod followed is given in the column headed "P". In the table Ph=phenyl, which may be substituted as indicated; e.g. 3,4—$Cl_2$—Ph— means 3,4-dichlorophenyl.

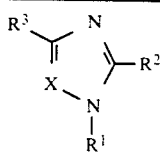

| Cpd no. | $R^3$ | $R^1$ | X | $R^2$ | P | m.p. (°) |
|---|---|---|---|---|---|---|
| 10 | 4-Br—Ph— | $SO_2NMe_2$ | CH | CN | 2 | 158-74 |
| 11 | 4-MeO—Ph— | $SO_2NMe_2$ | CH | CN | 2 | 152-4 |
| 12 | 4-$CF_3$—Ph— | $SO_2NMe_2$ | CH | CN | 2 | 166-8 |
| 13 | 3,4-$Cl_2$—Ph— | $SO_2NMe_2$ | CH | CN | 2 | 145-6 |
| 14 | 2,4-$Cl_2$-3-CN—Ph— | $SO_2NMe_2$ | CH | CN | 2 | 197-201 |
| 15 | 4-Cl—Ph— | $SO_2NMe_2$ | CH | CN | 2 | 170-1 |
| 16 | 3,4-$Cl_2$—Ph— | $SO_2NMe_2$ | CH | $CSNH_2$ | 3 | 184-6 |
| 17 | 4-$CF_3$—Ph— | $SO_2NMe_2$ | CH | $CSNH_2$ | 3 | 183-5 |
| 18 | 4-F—Ph— | $SO_2NMe_2$ | CH | $CSNH_2$ | 3 | 191-3 |
| 19 | 4-Cl—Ph— | $SO_2NMe_2$ | CH | $CSNH_2$ | 3 | 194-5 |
| 20 | 2,3,4-$Cl_3$—Ph— | $SO_2NMe_2$ | CH | $CSNH_2$ | 3 | 161-3 |
| 21 | 4-Br—Ph— | $SO_2NMe_2$ | CH | $CSNH_2$ | 3 | 188-9 |
| 22 | 4-$CF_3$— | $SO_2NMe_2$ | CH | CN | 2 | 86-7 |
| 23 | 2,4-$F_2$—Ph— | $SO_2NMe_2$ | CH | CN | 2 | 161-3 |
| 24 | 3-$CF_3$—Ph— | $SO_2NMe_2$ | CH | CN | 2 | 144-5 |
| 25 | 2-$CF_3$—Ph— | $SO_2NMe_2$ | CH | CN | 2 | 76-77.5 |
| 26 | 2,4-$Cl_2$—Ph— | $SO_2N\diagup\diagdown O\diagdown\diagup$ | CH | CN | 2 | 169-70 |
| 27 | 2,6-$Cl_2$—PhCO— | $SO_2NMe_2$ | CH | CN | 2 | 166-7 |
| 28 | 5-Cl-thien-2-yl | $SO_2NMe_2$ | CH | CN | 2 | 138-40 |
| 29 | 2,4,6-$Me_3$—PhCO— | $SO_2NMe_2$ | CH | CN | 2 | 149-51 |
| 30 | 4-F—Ph— | $SO_2NMe_2$ | CH | CN | 2 | 172-7 |
| 31 | 2,3,4-$Cl_3$—Ph— | $SO_2NMe_2$ | CH | CN | 2 | 143-8 |
| 32 | Ph— | $SO_2NMe_2$ | N | CN | 1 | 107-11 |
| 33 | 2,5-$Cl_2$-thien-3-yl | $SO_2NMe_2$ | CH | CN | 2 | 118-9 |
| 34 | Ph— | $SO_2NMe_2$ | CH | CN | 1 | 104-5 |
| 35 | 4-$NO_2$—Ph— | $SO_2NMe_2$ | CH | CN | 5 | 202-8 |
| 36 | 2-$CF_3$—Ph— | $SO_2NMe_2$ | CH | $CSNH_2$ | 3 | 113-5 |
| 37 | 3-$CF_3$—Ph— | $SO_2NMe_2$ | CH | $CSNH_2$ | 3 | 193-5 |
| 38 | 2,4-$F_2$—Ph— | $SO_2NMe_2$ | CH | $CSNH_2$ | 3 | 168-70 |
| 39 | 2,3,4-$Cl_3$—Ph— | $P(=O)(NMe_2)_2$ | CH | CN | 7 | 143-8 |
| 40 | 2,4,5-$Cl_3$—Ph— | $SO_2NMe_2$ | CH | CN | 2 | 182-4 |
| 41 | 2-Cl—Ph— | $SO_2NMe_2$ | CH | CN | 2 | 148-9 |
| 42 | 2,4-$Cl_2$—Ph— | $SO_2NMe_2$ | CH | CN | 2 | 172-3 |
| 43 | 2,4-$Me_2$—Ph— | $SO_2NMe_2$ | CH | CN | 2 | 100-1 |
| 44 | 2-F—Ph— | $SO_2NMe_2$ | CH | CN | 2 | 126-8 |
| 45 | 3-F—Ph— | $SO_2NMe_2$ | CH | CN | 2 | 122-3 |
| 46 | Me | $SO_2NMe_2$ | CH | CN | 2 | 88-90 |
| 47 | 3-Cl—Ph— | $SO_2NMe_2$ | CH | CN | 2 | 118-20 |
| 48 | H | $SO_2NMe_2$ | C(Me) | CN | 2 | 118-20 |
| 49 | 4-CN—Ph— | $SO_2NMe_2$ | CH | CN | 2 | 226-33 |
| 50 | 4-Cl—PhN(Me)$SO_2$— | $SO_2NMe_2$ | CH | CN | 2 | 194-7 |
| 51 | $Me_2NSO_2$— | $SO_2NMe_2$ | CH | CN | 2 | 154-5 |
| 52 | 4-MeO—Ph— | $SO_2NMe_2$ | N | CN | 2 | 135-6 |
| 53 | 4-CN | $SO_2NMe_2$ | CH | CN | 2 | 110-2 |
| 54 | 2,3,4-$Cl_3$—Ph— | $SO_2NMe_2$ | CH | CH=NOMe | 11 | 182-4 |
| 55 | 2,4-$Me_3$—Ph— | $SO_2NMe_2$ | N | CN | 2 | 121-3 |
| 56 | $Ph_2C(OEt)$— | $SO_2NMe_2$ | C(Me) | CN | 2 | 165-6 |
| 57 | 2,4-$Cl_2$—Ph— | $SO_2NMe_2$ | C(CN) | CN | $9^1$ | 105 |
| 58 | 4-Br—Ph— | $SO_2NMe_2$ | C(COOEt) | CN | $9^2$ | 110-3 |
| 59 | 4-Cl—Ph—CH=CH— | $SO_2NMe_2$ | CH | CN | 2 | 93-4 |
| 60 | H | $SO_2NMe_2$ | C(Ph) | CN | 2 | 98-106 |

-continued

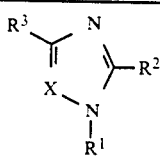

| Cpd no. | R³ | R¹ | X | R² | P | m.p. (°) |
|---|---|---|---|---|---|---|
| 61 | PhCO— | SO₂NMe₂ | CH | CN | 10 | 145-7 |
| 62 | 2,3,4-Cl₃—Ph— | SO₂NMe₂ | CH | (N-containing heterocycle with S, O, O) | 8 | 157-9 |
| 63 | PhS— | SO₂NMe₂ | CH | CN | 2 | 83.5-84 |
| 66 | 2-CF₃—PhCO— | SO₂NMe₂ | CH | CN | 2 | 135-7 |
| 67 | 4-Cl—PhCO— | SO₂NMe₂ | CH | CN | 2 | 166-170 |
| 68 | 3-Cl—PhCO— | SO₂NMe₂ | CH | CN | 2 | 162-3 |
| 69 | 4-F—PhCO— | SO₂NMe₂ | CH | CN | 2 | 133.5-135 |
| 70 | 4-Me—PhCO— | SO₂NMe₂ | CH | CN | 2 | 127-8 |
| 71 | 2-Me—PhCO— | SO₂NMe₂ | CH | CN | 2 | 110-3 |
| 72 | 2-MeO—PhN(Me)SO₂— | SO₂NMe₂ | CH | CN | 2 | 152-152.5 |
| 73 | PhN(Me)SO₂— | SO₂NMe₂ | CH | CN | 2 | 164-5 |
| 74 | PhN(Et)SO₂— | SO₂NMe₂ | CH | CN | 2 | 148-150 |
| 75 | 2-Me—PhN(Et)SO₂— | SO₂NMe₂ | CH | CN | 2 | 118-120 |
| 76 | 2,4-Cl₂—PhN(Me)SO₂— | SO₂NMe₂ | CH | CN | 2 | 149-150 |
| 77 | 4-Cl—PhN(Et)SO₂— | SO₂NMe₂ | CH | CN | 2 | 138-140 |
| 78 | 3-Cl—PhN(Me)SO₂— | SO₂NMe₂ | CH | CN | 2 | 141-143 |
| 79 | 4-Cl—PhN(Pr)SO₂— | SO₂NMe₂ | CH | CN | 2 | 120-122 |
| 80 | 4-F—PhN(Me)SO₂— | SO₂NMe₂ | CH | CN | 2 | 176-178 |
| 81 | 3-CF₃—PhCO— | SO₂NMe₂ | CH | CN | 2 | 131 |

Notes:
¹reaction carried out using p-tosyl cyanide
²reaction carried out using ethyl chloroformate

EXAMPLE 13

Acetyl chloride (0.97 g) was added dropwise to a mixture of a solution of compound 20 (2.56 g) in acetone (20 ml) with stirring and cooling. The mixture was heated under reflux for 30 minutes and then evaporated. The residue was extracted with dichloromethane and the extract washed with water, dried, evaporated and purified by column chromatography to give 2-(N-acetylthiocarbamoyl)-1-(dimethylsulphamoyl)-4-(2,3,4-trichlorphenyl)imidazole, m.p. 132°-134°. (Compound 64).

EXAMPLE 14

A mixture of compound 63 (0.31 g) in dichloromethane (25 ml) and m-chloroperbenzoic acid (0.54 g of 80g) was stirred at room temperature for 3 hours. The mixture was extracted with water and then aqueous sodium carbonate, and the organic phase dried and evaporated. The residue was recrystallised from toluene/hexane to give 2-cyano-4-(phenylsulphonyl)-1-(dimethylsulphamoyl)imidazole, m.p. 164°-165.5° (dec.). (Compound 65)

Preparation of starting materials

The following methods illustrate typical ways of preparing starting materials.

Method A as used for starting material of Example 1

A mixture of 4-(2,4-dichlorophenyl)-1H-imidazole (12.14 g), triethylamine (13 ml) and dimethylsulphamoyl chloride (7.5 ml) in tetrahydrofuran (50 ml) was stirred for 18 hours at room temperature and then heated under reflux until almost no starting material remained. The organic phase was diluted with ethyl acetate (300 ml), washed with dilute hydrochloric acid, water and aqueous sodium bicarbonate, dried and the solvent evaporated to give an oily solid which was treated to flash column chromatography and the product recrystallised to give 4-(2,4-dichlorophenyl)-1-(dimethylsulphamoyl)imidazole, m.p. 169°-171°.

Method B as used for starting material of Compounds 4 and 35

A mixture of compound 34 (6.72 g) and nitronium tetrafluoroborate (98 ml of 0.5M in sulpholane) in sulpholane 25 ml was stirred for 16 hours at room temperature. It was then added to ice/water and filtered. The solid from the filtration was washed with water and dried. This was treated to flash column chromatography (using ethyl acetate/hexane as eluent to give 2-cyano-4-(4-nitrophenyl)-1H-imidazole, m.p. 230° (dec.). The filtrate was extracted with ethyl acetate and the extract worked up in usual manner and the residue treated to flash column chromatography (using ethyl ace ate/hexane as eluent to give 2-cyano-4-(2-nitrophenyl)-1H-imidazole. m.p. 166°-170° (dec.).

Method C as used for starting material of Example 6

A mixture of 2-bromo-2',4',6'-trichloroacetophenone (42 g) and formamide (200 ml) was heated under reflux for 2 hours, with stirring. It was cooled, poured into 2M hydrochloric acid, heated on a steam bath, filtered and the filtrate made basic with ammonia. The solid was collected and dried under reduced pressure to give crude 4-(2,4,6-trichlorobenzoyl)imidazole. This was then treated with dimethylsulphamoyl chloride in a similar manner to that described in Example 1, to give 1-(dimethylsulphamoyl)-4-(2,4,6-trichlorobenzoyl)imidazole.

Method D as used for starting material of Example 7

A solution of compound 1 (4 g) in tetrahydrofuran (40 ml) and water (15ml) was heated under reflux with in turn aqueous sodium hydroxide and methanolic potassium carbonate until tlc showed that the reaction was complete. The reaction mixture was neutralised with hydrochloric acid and the precipitate collected, washed with water, dried and purified by flash column chromatography (using light petroleum (b.p. 60°–80°)/ethyl acetate (3:1) as eluent) to give 2-cyano-4-(2,4-dichlorophenyl)imidazole.

Method E as used for starting material of Example 10

1-(Dimethylsulphamoyl)-4-(2,4,6-trichlorobenzoyl)imidazole (2.6 g) in dry tetrahydrofuran (15 ml) was added over 30 seconds to lithium aluminium hydride (110 mg) in dry tetrahydrofuran (15 ml) with cooling. The mixture was stirred at 5° for 30 minutes. Water (0.110 ml ), aqueous sodium hydroxide (15%: 0.110 ml) and water (0.330 ml) were added and the mixture stirred for 15 minutes at room temperature. The mixture was filtered and the precipitate washed with tetrahydrofuran. The filtrate and washings were evaporated under reduced pressure and the residue washed with diisopropyl ether and dried under reduced pressure to give 1-(dimethylsulphamoyl)-4-(2,4,6-trichloro-α-hydroxybenzyl)imidazole, as an off white solid. To this product (1.92 g) in dry tetrahydrofuran (40 ml) was added sodium hydride (170 mg; 80g in oil), with stirring, under nitrogen. Trimethylsilyl chloride (0.7 ml) was added to this mixture at 30° to give the trimethyl silyl ether. The mixture was then cooled to −70° and butyllithium (2.2 ml; 2 5M in hexane) added. The mixture was stirred at −78° for 30 minutes, dimethylformamide (0.5 ml) added and the mixture allowed to warm to room temperature. The mixture was poured into ice/water, stirred for 30 minutes and the solid collected and dried to give crude 1-(dimethylsulphamoyl)-2-formyl-4-[(2,4,6-trichloro-α-(trimethylsilyloxy)benzyl]imidazole. This was then then treated with hydroxylamine hydrochloride in a similar manner to step (b) in Example 1, to give crude 1-(dimethylsulphamoyl)-2-(hydroxyiminomethyl)-4-(2,4,6-trichloro-α-hydroxybenzyl)imidazole. This was then treated with trifluoroacetic anhydride in a similar manner to step (c) in Example 1, to give crude 2-cyano-1-(dimethylsulphamoyl)-4-(2,4,6-trichloro-α-hydroxybenzyl)imidazole, as an off white solid.

Method F was used for starting material of Compound 56

Ethyl 5-methylimidazole-4-carboxylate was converted by a Grignard reaction, using phenylmagnesium bromide, to 4-[ethoxy(diphenyl)methyl]-5-methylimidazole, m.p. 205°. This was then treated with dimethylsulphamoyl chloride in a similar manner to that described in Example 1, to give 1-dimethylsulphamoyl-4-[ethoxy(diphenyl)methyl]-5-methylimidazole, m.p. 150°.

Method G as used for starting material of Compound 50

Imidazole-4-sulphonyl chloride was reacted with 4-chloro-N-methylaniline to give 4-[N-(4-chlorophenyl)-N-methylsulphamoyl]imidazole, m.p. 217°–9°. This was then treated with dimethylsulphamoyl chloride in a similar manner to that described in Example 1, to give 1-dimethylsulphamoyl-4-[N-(4-chlorophenyl)-N-methylsulphamoyl]imidazole, m.p. 131.5°–132°.

Method H as used for starting material of Compound 60

N-Benzylidene-N',N'-dimethylsulphamide (6.36 g) was stirred with p-toluenesulphonylmethyl isocyanide (9.75 g ) and potassium carbonate (8.28 g) in methanol and dimethoxyethane for 18 hours. The mixture was filtered and the filtrate evaporated and recrystallised from ethyl acetate/hexane to give crude 1-dimethylsulphamoyl-5-phenylimidazole.

For Compound 14, the starting material was prepared by reacting the starting material used in Example 1 with two moles of butyllithium/dimethylformamide to give 4-(2,4-dichloro-3-formylphenyl)-1-(dimethylsulphamoyl)-2-formylimidazole which in turn was reacted with two moles of hydroxylamine hydrochloride to give 4-[2,4-dichloro-3-(hydroxyiminomethyl)phenyl]-1-(dimethylsulphamoyl)-2-(hydroxyiminomethyl)imidazole. This was reacted with two equivalents of trifluoroacetic anhydride to give the desired product.

For Compound 63, the starting material was prepared according to the method described in Tetrahedren, 1986, 42, 2351-8.

Other starting materials were either known or prepared by one of these or similar methods. Generally they were not purified so no physical data are given.

TEST EXAMPLE

The compounds of the invention were subjected (o various tests.

(a) Foliar tests

Compounds are assessed for activity against one or more of the following:
*Erysiphe graminis*: barley powdery mildew (EG)
*Plasmopara viticola*: vine downy mildew (PV)
*Pyricularia oryzae*: rice blast (PO)
*Botrytis cinerea*: grey mould of tomato (BC)
*Venturia inaequalis*: apple scab (VI)
*Phytophthora infestans*: late tomato blight (PI)

Aqueous solutions or dispersions of the compounds at the desired concentration, including a wetting agent, were sprayed onto the appropriate plant and then inoculated by spraying with spore suspensions of the fungi or by dusting or shaking diseased material over the treated plants for the Erysiphe spp. Plants were then kept under controlled environment conditions suitable for maintaining plant growth and development of the disease. After an appropriate time, the degree of infection of the leaf surface was visually estimated.

Compounds were considered active if they gave greater than 50% control of the disease at a concentration of 125 ppm (w/v) or less.

(b) Soil pathogen test

In these tests compounds were assessed for activity against *Rhizoctonia solani* (RS)

Flasks containing maize meal/sand were inoculated with the test fungus and then incubated. The maize meal/sand cultures were used to infest potting compost which was then put into plastic pots. Aqueous solutions or dispersions of the compounds, including a wetting agent, were added to the pots to give a desired concentration of compound in each pot. Control pots were set up by adding similar solutions or dispersions without the test compound. Immediately after application of the test compound each pot was sown with a number of cabbage seeds. The seeds were covered with treated infested soil and the pots incubated under controlled environment conditions suitable for plant growth and development of the disease. The number of emerged cabbage seedlings is counted and percentage disease control calculated by comparison with the untreated infested pots.

Compounds were considered active if they gave greater than 50% control of the disease at a concentration of 100 parts by weight of compound or less per million parts by volume of soil.

Activities were demonstrated as follows (+ = active).

| Compound No. | EG | PO | PI | PV | BC | VI | RS |
|---|---|---|---|---|---|---|---|
| 1 | + |  | + | + |  |  |  |
| 2 |  |  | + | + |  |  |  |
| 3 |  |  | + | + |  |  |  |
| 4 | + |  | + |  |  |  |  |
| 5 |  |  | + | + |  |  |  |
| 6 |  |  | + |  |  |  |  |
| 7 | + |  |  | + |  |  |  |
| 8 |  |  | + |  | + |  |  |
| 9 |  |  | + |  |  |  |  |
| 10 |  |  | + | + |  |  |  |
| 11 |  |  |  |  | + |  |  |
| 12 |  |  | + |  |  |  |  |
| 13 |  |  | + |  |  |  |  |
| 14 | + |  | + | + |  |  |  |
| 15 |  | + | + |  |  |  |  |
| 16 |  |  | + | + |  |  |  |
| 17 |  |  | + |  |  |  |  |
| 18 |  |  | + |  |  |  |  |
| 19 |  | + | + |  |  |  |  |
| 20 |  |  | + | + | + |  |  |
| 21 |  | + | + |  |  |  |  |
| 22 |  |  | + | + |  |  |  |
| 23 |  |  | + |  |  |  | + |
| 24 |  |  | + |  |  | + |  |
| 25 |  |  | + | + |  | + |  |
| 26 |  |  |  |  | + |  |  |
| 27 |  |  | + |  |  |  |  |
| 28 |  | + | + | + |  |  |  |
| 29 | + |  | + |  |  |  |  |
| 30 |  | + | + | + |  |  |  |
| 31 | + |  | + | + | + |  |  |
| 32 |  |  | + |  |  |  |  |
| 33 |  |  | + |  |  |  |  |
| 34 |  |  | + |  |  |  |  |
| 35 | + |  | + |  |  |  |  |
| 36 |  |  | + |  |  |  |  |
| 37 |  |  | + |  |  |  |  |
| 38 |  |  | + |  |  |  |  |
| 39 |  |  | + |  |  |  |  |
| 40 |  |  | + |  |  |  |  |
| 41 |  |  | + |  |  |  |  |
| 42 |  |  | + |  |  |  |  |
| 43 |  |  | + |  |  |  |  |
| 44 |  |  | + |  |  |  |  |
| 45 |  |  | + |  |  |  |  |
| 46 | + |  |  |  |  |  |  |
| 47 |  |  | + |  |  |  |  |
| 48 |  | + |  |  |  |  |  |
| 49 |  |  | + |  |  |  |  |
| 50 |  |  | + |  |  |  |  |
| 51 |  |  | + |  |  |  |  |
| 52 |  |  | + |  |  |  |  |
| 53 |  |  | + |  |  |  |  |
| 54 |  |  | + |  |  | + |  |
| 55 |  |  | + |  |  |  |  |
| 56 |  |  | + |  |  |  |  |
| 57 |  |  | + |  |  |  |  |
| 58 |  |  | + |  |  |  |  |
| 59 |  |  | + |  |  |  |  |
| 60 |  |  | + |  |  |  |  |
| 63 |  |  | + |  |  |  |  |
| 65 |  |  | + |  |  |  |  |
| 66 |  |  | + | + |  |  |  |
| 67 |  |  | + | + |  |  |  |
| 68 |  |  | + | + |  |  |  |
| 69 |  |  | + | + |  |  |  |
| 70 |  |  | + | + |  |  |  |
| 71 |  |  | + | + |  |  |  |
| 72 |  |  | + | + |  |  |  |
| 73 |  |  | + | + |  |  |  |
| 74 |  |  | + | + |  |  |  |
| 75 |  |  | + | + |  |  |  |
| 76 |  |  | + | + |  |  |  |
| 77 |  |  | + | + |  |  |  |
| 78 |  |  | + | + |  |  |  |
| 79 |  |  | + |  |  |  |  |
| 80 |  |  | + |  |  |  |  |
| 81 |  |  | + |  |  |  |  |

We claim:

1. A compound of formula I

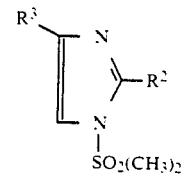

in which $R^2$ is CN or $-C(S)NHR^9$; $R^3$ is arylcarbonyl, in which the aryl group is phenyl, substituted by one or more of the same or different groups, selected from the group consisting of cyano, alkyl, trifluoromethyl, nitro and alkoxy, or alkylaryl-sulfamoyl, in which the aryl group is phenyl, optionally substituted by one or more of the same or different groups, selected from the group consisting of halogen, cyano, alkyl, trifluoromethyl, nitro and alkoxy; $R^9$ is hydrogen or alkanoyl; and in any group which is or includes alkyl contains up to 4 carbon atoms.

2. A compound according to claim 1, in which $R^2$ is cyano or thiocarbamoyl.

3. A compound according to claim 2, in which $R^3$ is benzoyl, substituted by up to three groups, selected from the group consisting of methyl, trifluoromethyl, nitro and methoxy.

4. A compound according to claim 3, in which $R^2$ is cyano and $R^3$ is benzoyl substituted by trifluoromethyl.

5. A fungicidal composition comprising an effective amount of a compound as claimed in claim 1, in admixture with an agriculturally acceptable diluent or carrier.

6. A fungicidal composition comprising an effective amount of a compound as claimed in claim 2, in admixture with an agriculturally acceptable diluent or carrier.

7. A fungicidal composition comprising an effective amount of a compound as claimed in claim 3, in admixture with an agriculturally acceptable diluent or carrier.

8. A fungicidal composition comprising an effective amount of a compound as claimed in claim 4, in admixture with an agriculturally acceptable diluent or carrier.

9. A method of combating phytopathogenic fungi which comprises applying to the fungus or its locus an effective amount of a compound claimed in claim 1.

10. A method of combating phytopathogenic fungi which comprises applying to the fungus or its locus an effective amount of a compound claimed in claim 2.

11. A method of combating phytopathogenic fungi which comprises applying to the fungus or its locus an effective amount of a compound claimed in claim 3.

12. A method of combating phytopathogenic fungi which comprises applying to the fungus or its locus an effective amount of a compound claimed in claim 4.

* * * * *